US008752546B2

(12) United States Patent
Acker et al.

(10) Patent No.: US 8,752,546 B2
(45) Date of Patent: Jun. 17, 2014

(54) SYSTEM AND METHOD FOR MOBILIZING OCCLUSIONS FROM A BREATHING TUBE

(75) Inventors: Jaron Matthew Acker, Madison, WI (US); Andreas Tzanet Akis, Helsinki (FI); Andrew Phillip Levi, Madison, WI (US)

(73) Assignee: General Electric Company, Schenectady, NY (US)

( * ) Notice: Subject to any disclaimer, the term of this patent is extended or adjusted under 35 U.S.C. 154(b) by 1284 days.

(21) Appl. No.: 12/107,907

(22) Filed: Apr. 23, 2008

(65) Prior Publication Data
US 2009/0266360 A1 Oct. 29, 2009

(51) Int. Cl.
*A61M 16/00* (2006.01)

(52) U.S. Cl.
USPC ............. 128/204.21; 128/204.23; 128/204.18

(58) Field of Classification Search
USPC ............. 128/205.19, 204.18, 204.23, 207.14, 128/204.21; 604/540, 541
See application file for complete search history.

(56) References Cited

U.S. PATENT DOCUMENTS

| 4,178,940 | A | * | 12/1979 | Au | 128/207.15 |
|---|---|---|---|---|---|
| 4,550,726 | A | * | 11/1985 | McEwen | 128/202.22 |
| 4,573,460 | A | * | 3/1986 | Szachowicz et al. | 128/200.26 |
| 5,007,420 | A | * | 4/1991 | Bird | 128/200.14 |
| 5,881,717 | A | * | 3/1999 | Isaza | 128/202.22 |
| 6,390,092 | B1 | * | 5/2002 | Leenhoven | 128/204.23 |
| 6,622,726 | B1 | | 9/2003 | Du | |
| 6,860,265 | B1 | * | 3/2005 | Emerson | 128/205.12 |
| 7,191,780 | B2 | | 3/2007 | Faram | |
| 7,320,320 | B2 | | 1/2008 | Berthon-Jones | |
| 2006/0162727 | A1 | * | 7/2006 | Biondi et al. | 128/204.21 |
| 2007/0277827 | A1 | * | 12/2007 | Bordewick et al. | 128/205.25 |
| 2008/0060656 | A1 | * | 3/2008 | Isaza | 128/207.16 |
| 2009/0007914 | A1 | * | 1/2009 | Bateman | 128/204.23 |
| 2011/0087123 | A9 | * | 4/2011 | Choncholas et al. | 600/538 |

FOREIGN PATENT DOCUMENTS

| EP | 0425092 A1 | 5/1991 |
|---|---|---|
| WO | 9841268 A1 | 9/1998 |
| WO | WO9841269 | 9/1998 |
| WO | 2006034549 A2 | 4/2006 |

OTHER PUBLICATIONS

Second Office Action issued in connection with Swedish Patent Application No. 0950264-2, Sep. 15, 2010.

* cited by examiner

*Primary Examiner* — Justine Yu
*Assistant Examiner* — Valerie L Skorupa (57) ABSTRACT

A method for mobilizing an occlusion from a breathing tube is presented. The method includes automatically mobilizing the occlusion from the breathing tube by regulating an inspiratory flow, an expiratory flow, or a combination thereof, where the breathing tube is configured to operationally couple a patient to a ventilation system, and where the ventilation system is configured to provide artificial respiration to the patient.

21 Claims, 6 Drawing Sheets

SYSTEM AND METHOD FOR MOBILIZING OCCLUSIONS FROM A BREATHING TUBE

BACKGROUND

This disclosure relates generally to clinical workflow, and more particularly to a design of a method configured to aid in enhancing clinical workflow.

In a caregiving facility, such as a hospital, and more particularly, in an Intensive Care Unit (ICU), it may be desirable to provide artificial ventilation to a majority of patients. Patients are intubated and ventilated in order to treat and manage respiratory failures, such as asthma, pneumonia, pulmonary edema, pulmonary embolism, chronic bronchitis, post-operative hypoxemia, chest injuries and chronic lung disease. Along with patients suffering from respiratory failure, certain patients may need ventilatory support for other medical reasons. By way of example, post-operative ICU patients and certain maxillofacial surgical patients may also require a period of post operative care/management in the ICU, during which time the patients are typically kept sedated and ventilated.

Traditionally, artificial ventilation is provided via use of a ventilator. More particularly, artificial ventilation is provided via positive pressure ventilation, where gas is delivered under positive pressure, allowing alveoli expansion and gas exchange. Once a patient has been identified as needing artificial ventilation, they are intubated and placed on a ventilator and ventilated using positive pressure. Gases are delivered to the patient using pressure to inflate the lungs, expand the alveoli and allow for gas exchange and oxygenation. In other words, the goal of conventional artificial ventilation is to use positive pressure to deliver gas and achieve respective ventilatory goals, thereby maintaining suitable pressure and flow of gases inspired and expired by the patient.

As will be appreciated, the ventilator is generally coupled to the patient via a breathing tube. The breathing tube may include a tracheal tube or an endotracheal tube, for example. Unfortunately, a problem commonly encountered during use of the breathing tube includes occlusions in the breathing tube. More particularly, the breathing tube may become occluded with a mucus plug, secretions, and/or other debris, thereby posing a health risk to the patient and diminishing the effectiveness of the ventilator.

Currently available techniques entail manual detection of the occlusions in the breathing tube. Once the occlusions are detected, a clinician, such as a nurse or a respiratory therapist, may disconnect the ventilator from the patient and suction the breathing tube periodically to remove mucus and other occlusions from the breathing tube. However, this suctioning procedure is known to be cumbersome and causes great discomfort to the patient.

An alternative approach to clearing mucus plugs and/or other debris in the breathing tube includes use of a suction catheter. As will be appreciated, the suction catheter is a flexible, long tube attached to one end to the breathing tube. The other end of the suction catheter is connected to a collection container (suction canister) and a device that generates suction. Critically ill or injured patients using a breathing (endotracheal) tube or a tracheostomy tube typically need occasional suctioning to remove secretions from the airway. The respiratory therapist, nurse, or ICU technician may suction the patient by inserting the suction catheter into the breathing tube in order to keep the breathing tube clear of secretions and prevent plugging of the airways. In addition, frequency of suctioning is determined by the amount of secretions that the patient produces. The breathing tube is suctioned whenever fluid builds up in the lungs. Unfortunately, use of the suction catheter is a painful procedure and is known to cause trauma to the patient.

Furthermore, certain other techniques entail manual detection of occlusions in the breathing tube followed by manual determination of change in settings on the ventilator to facilitate clearance of occlusions in the breathing tube. However, this procedure is laborious and time consuming, causing extended discomfort to the patient.

It may therefore be desirable to develop a design of a method that may be configured to advantageously aid in automatically mobilizing any occlusions out of breathing tube associated with the patient, thereby enhancing the clinical workflow and reducing patient discomfort. More particularly, it may be desirable to reduce frequency of clinician intervention to clear occlusions building up in the breathing tube, thereby minimizing discomfort to the patient.

BRIEF DESCRIPTION

In accordance with aspects of the present technique, a method for mobilizing an occlusion from a breathing tube is presented. The method includes automatically mobilizing the occlusion from the breathing tube by regulating an inspiratory flow, an expiratory flow, or a combination thereof, where the breathing tube is configured to operationally couple a patient to a ventilation system, and where the ventilation system is configured to provide artificial respiration to the patient.

In accordance with further aspects of the present technique, an integrated ventilation system is presented. The integrated ventilation system includes a ventilation system configured to provide artificial respiration to a patient, wherein the ventilation system is operationally coupled to the patient via a breathing tube. In addition, the integrated ventilation system includes an occlusion mobilizing module configured to automatically mobilize an occlusion from the breathing tube by regulating an inspiratory flow, an expiratory flow, or a combination thereof.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
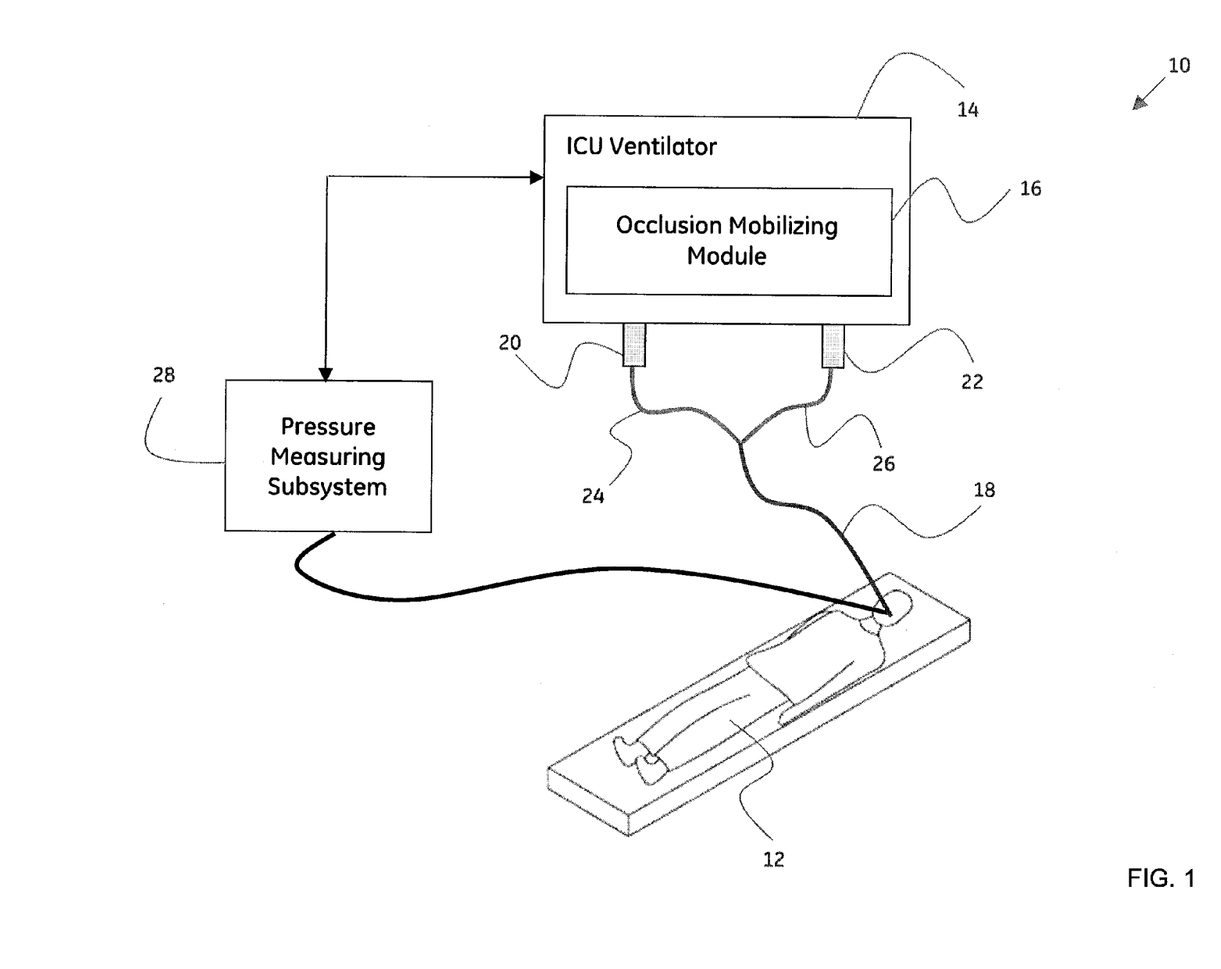
FIG. 1 is a block diagram of a ventilation system configured to automatically mobilize occlusions from a breathing tube, in accordance with aspects of the present technique.

FIG. 1 is a block diagram of an exemplary ventilation system 10 that may be configured to aid in mobilizing one or more occlusions from a breathing tube, where the breathing tube may be disposed in a patient 12, in accordance with aspects of the present technique. In other words, the exemplary ventilation system 10 may be configured to aid a traditional ICU ventilator in mobilizing occlusions from the patient 12, thereby enhancing clinical workflow by circumventing use of suction and/or a suction catheter to mobilize occlusions in the breathing tube, and minimizing discomfort to the patient 12.

The ventilation system 10 may generally be operationally coupled to the patient 12 via a breathing tube. Unfortunately, a problem commonly encountered during use of the breathing tube includes occlusions in the breathing tube. More particularly, the breathing tube may become occluded with a mucus plug and/or other debris, thereby causing discomfort to the patient 12 and diminishing the effectiveness of the ventilation system 10. According to exemplary aspects of the present technique, a module configured to advantageously aid a traditional ventilation system in automatically mobilizing any occlusions in the breathing tube, is presented.

Furthermore, in FIG. 1, the ventilation system 10 is shown as being operationally coupled to the patient 12. In one embodiment, the ventilation system 10 may include a ventilator 14, such as an ICU ventilator. As will be appreciated, the ICU ventilator 14 is a machine that may be configured to aid the patient 12 in breathing through a tube, such as a breathing tube 18, that is typically inserted into the trachea of the patient 12 via the mouth or nose of the patient 12, where the breathing tube 18 is operationally coupled to the ICU ventilator 14. It may be noted that the terms breathing tube and breathing circuit may be used interchangeably. Further, the ICU ventilator 14 may also include a first connector 20 and a second connector 22. The first connector 20 and the second connector 22 may be configured to aid in operationally coupling the ICU ventilator 14 to the patient 12 via the breathing tube 18.

As noted hereinabove, the patient 12 may be operationally coupled to the ICU ventilator 14 via the breathing tube 18. The breathing tube 18 may include an inspiratory branch 24 and an expiratory branch 26. In the embodiment illustrated in FIG. 1, breathing tube 18 is shown as being operationally coupled to the first connector 20 of the ICU ventilator 14 via the inspiratory branch 24. The ICU ventilator 14 may be configured to pump gas into the lungs of the patient 12 through the inspiratory branch 24. In a similar fashion, the breathing tube 18 is also shown as being operationally coupled to the second connector 22 of the ICU ventilator 14 via the expiratory branch 26. The ICU ventilator 14 may be configured to aid in the exhalation of gas from the lungs of the patient 12 through the expiratory branch 26.

Generally, the breathing tube 18 may be inserted through the mouth of the patient 12 and advanced into the patient's airway until a distal end (not shown in FIG. 1) of the breathing tube 18 passes through the patient's larynx (not shown in FIG. 1). As will be appreciated by those skilled in the art, the breathing tube 18 may become occluded or blocked by an occlusion (not shown in FIG. 1). The occlusion may include a mucus plug and/or other debris, for example. Furthermore, the occlusion may pose a serious health risk to the patient 12 and/or cause discomfort to the patient 12. Additionally, the occlusion may also diminish the effectiveness of the ventilator system 10.

According to exemplary aspects of the present technique, the ICU ventilator 14 may include an occlusion mobilizing module 16 configured to aid the ICU ventilator 14 in automatically mobilizing any occlusions from the breathing tube 18. In a presently contemplated configuration, the ICU ventilator 14 is shown as including the occlusion mobilizing module 16. However, in certain other embodiments, the occlusion mobilizing module 16 may include a standalone module configured for use with a ventilation system, such as the ventilation system 10 (see FIG. 1). The working of the occlusion mobilizing module 16 will be described in greater detail with reference to FIGS. 3-5. In addition, the ventilation system 10 may also include a pressure measuring subsystem 28, where the pressure measuring subsystem 28 may be configured to aid in measuring pressure of air that is pumped into the patient 12.

Figure 2:
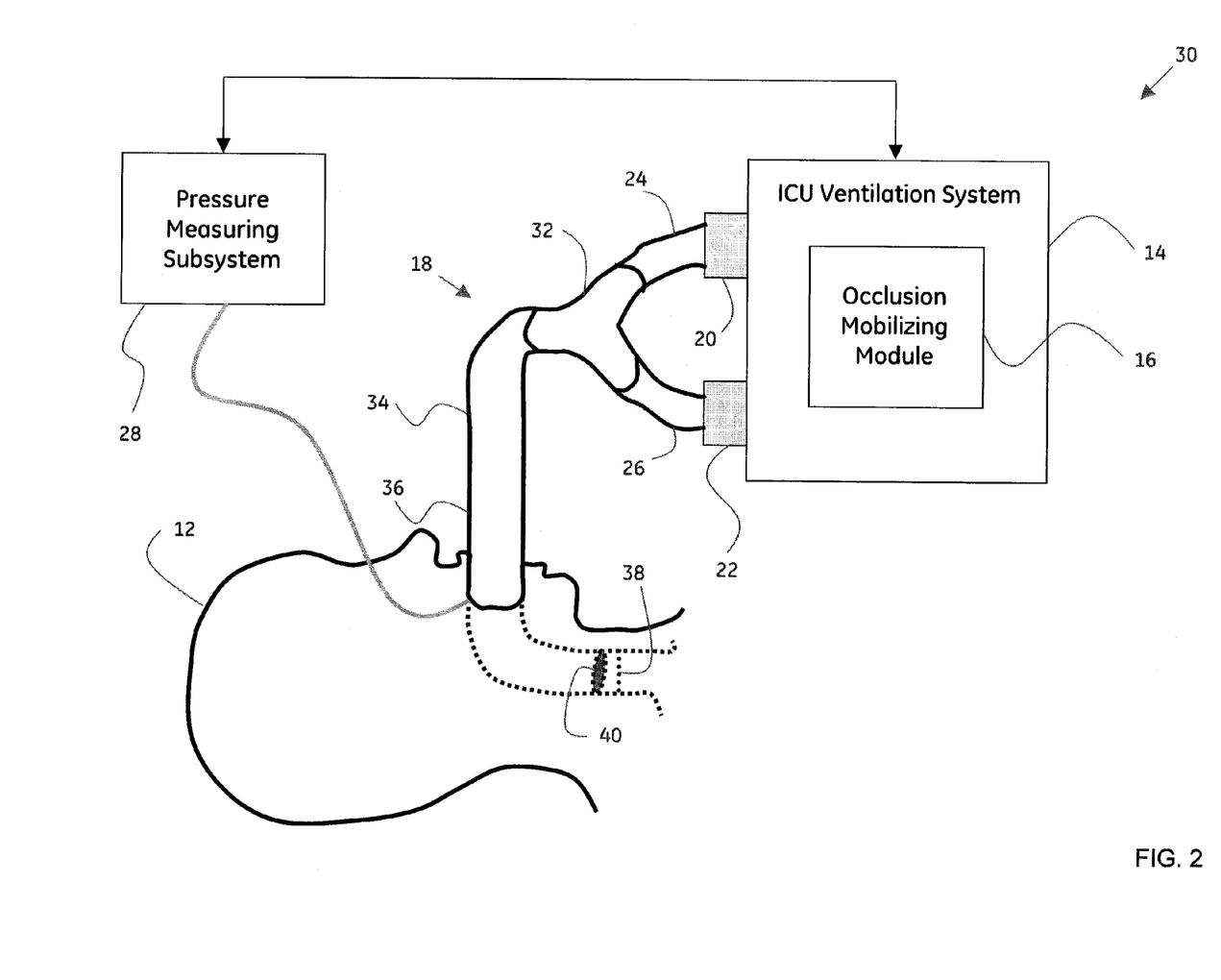
FIG. 2 is a block diagram of an embodiment of a ventilation system of FIG. 1, in accordance with aspects of the present technique.

Turning now to FIG. 2, a diagrammatic illustration of one embodiment 30 of the ventilation system 10 of FIG. 1 is illustrated. As previously noted with reference to FIG. 1, a ventilator, such as the ICU ventilator 14 (see FIG. 1) may be operationally coupled to the patient 12 via the breathing tube 18, for example. Further, the ICU ventilator 14 may include the first connector 20 (see FIG. 1) and the second connector 22 (see FIG. 1), where the first connector 20 may be configured to receive the inspiratory tube 24 of the breathing tube 18, while the second connector 22 may be configured to receive the expiratory tube 26 of the breathing tube 18, as previously noted. In addition, the breathing tube 18 may also include a Y-connector 32, a patient branch 34, and an interface 36. It may be noted that the interface 36 is a portion of the breathing tube 18 that is directly coupled with the patient 12. In certain embodiments, the interface 36 may include a tracheal tube or an endotracheal tube. In the embodiment illustrated in FIG. 2, the interface 36 is shown as including an endotracheal tube. However it should be appreciated that other known devices may also be implemented for the interface 36.

As noted hereinabove with reference to FIG. 1, the endotracheal tube 36 may be inserted through the patient's mouth and advanced into the patient's airway until a distal end 38 of the endotracheal tube 36 passes through the patient's larynx (not shown in FIG. 2). Furthermore, the endotracheal tube 36 may become occluded or blocked by an occlusion 40, where the occlusion 40 may include a mucus plug and/or other debris, for example. According to exemplary aspects of the present technique, the ICU ventilator 14 may include the occlusion mobilizing module 16 configured to aid the ICU ventilator 14 in automatically mobilizing any occlusions, such as the occlusion 40, from the breathing tube 18, as previously noted with reference to FIG. 1.

Currently available techniques typically entail manual operations to clear the breathing tube 18 of any occlusions, where the manual operations may include a suction operation and/or use of a suction catheter. However, use of the currently available techniques results in elevated levels of patient discomfort. Hence, it may be desirable to develop a method configured to automatically mobilize occlusions from the breathing tube 18, thereby reducing patient discomfort and enhancing clinical workflow.

Figure 3:
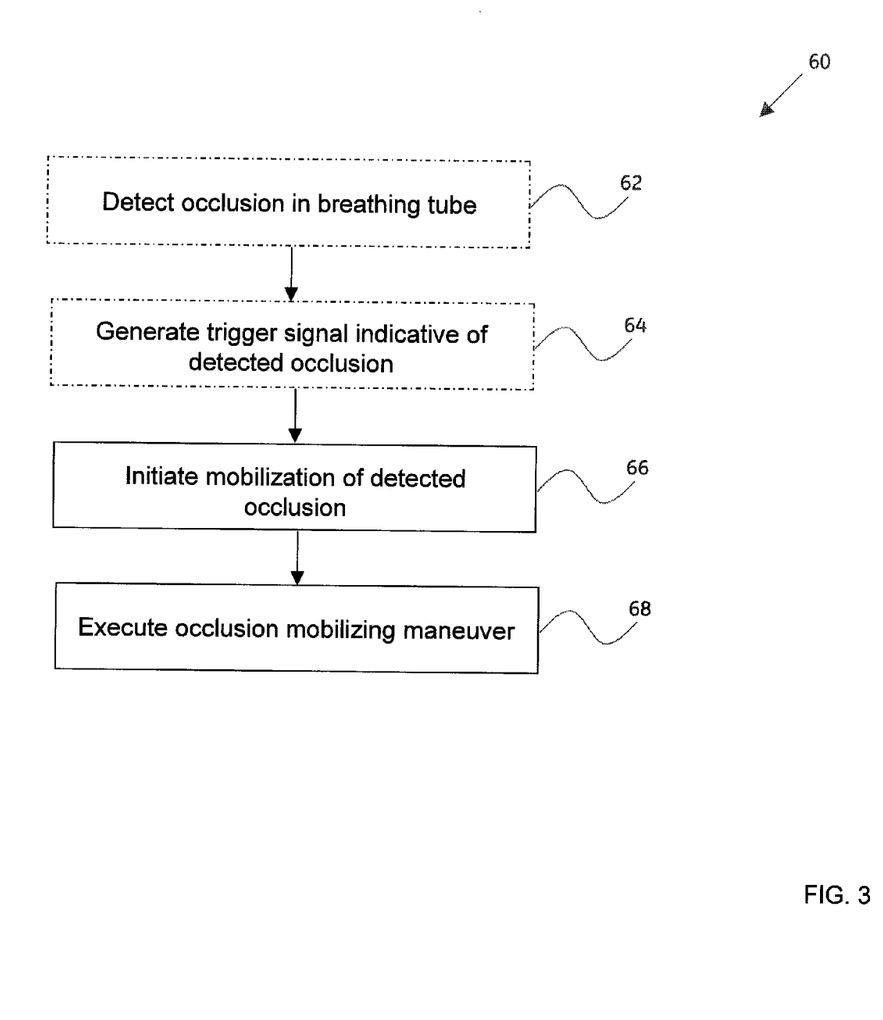
FIG. 3 is a flow chart illustrating an exemplary method for mobilizing occlusions from a breathing tube using the exemplary ventilation system of FIG. 1, in accordance with aspects of the present technique.

FIG. 3 is a flow chart 60 depicting an exemplary method for mobilizing an occlusion from a breathing tube, such as the breathing tube 18 (see FIG. 1). In a presently contemplated configuration, the occlusion mobilizing module 16 (see FIG.

1) may be configured to aid the ICU ventilator 14 (see FIG. 1) in performing the exemplary method for mobilizing an occlusion from the breathing tube.

The method starts at step 62 where one or more occlusions in a breathing tube may be detected. As previously noted, the occlusions in the breathing tube may include mucus plugs and/or other debris. Once the occlusion in the breathing tube is detected, a trigger signal may be generated, as indicated by step 64, where the trigger signal may be indicative of the detected occlusion. In certain embodiments, the trigger signal may include an alarm signal, where the alarm signal may be configured to alert hospital personnel, such as a clinician or a nurse, to the presence of an occlusion within the breathing tube.

Subsequently, at step 66, a maneuver for automatically mobilizing the occlusion from the breathing tube may be initiated. It may be noted that although FIG. 3 depicts the method for automatically mobilizing the occlusion from the breathing tube as including optional steps 62-64, the method for automatically mobilizing the occlusion from the breathing tube may also start at step 66. In other words, the maneuver for automatically mobilizing the occlusion from the breathing tube may be automatically initiated even in the absence of a trigger signal. More particularly, in certain embodiments, the maneuver for mobilizing occlusions from the breathing tube may be periodically executed, while in certain other embodiments, the maneuver for mobilizing occlusions from the breathing tube may be continually executed.

Figure 4:
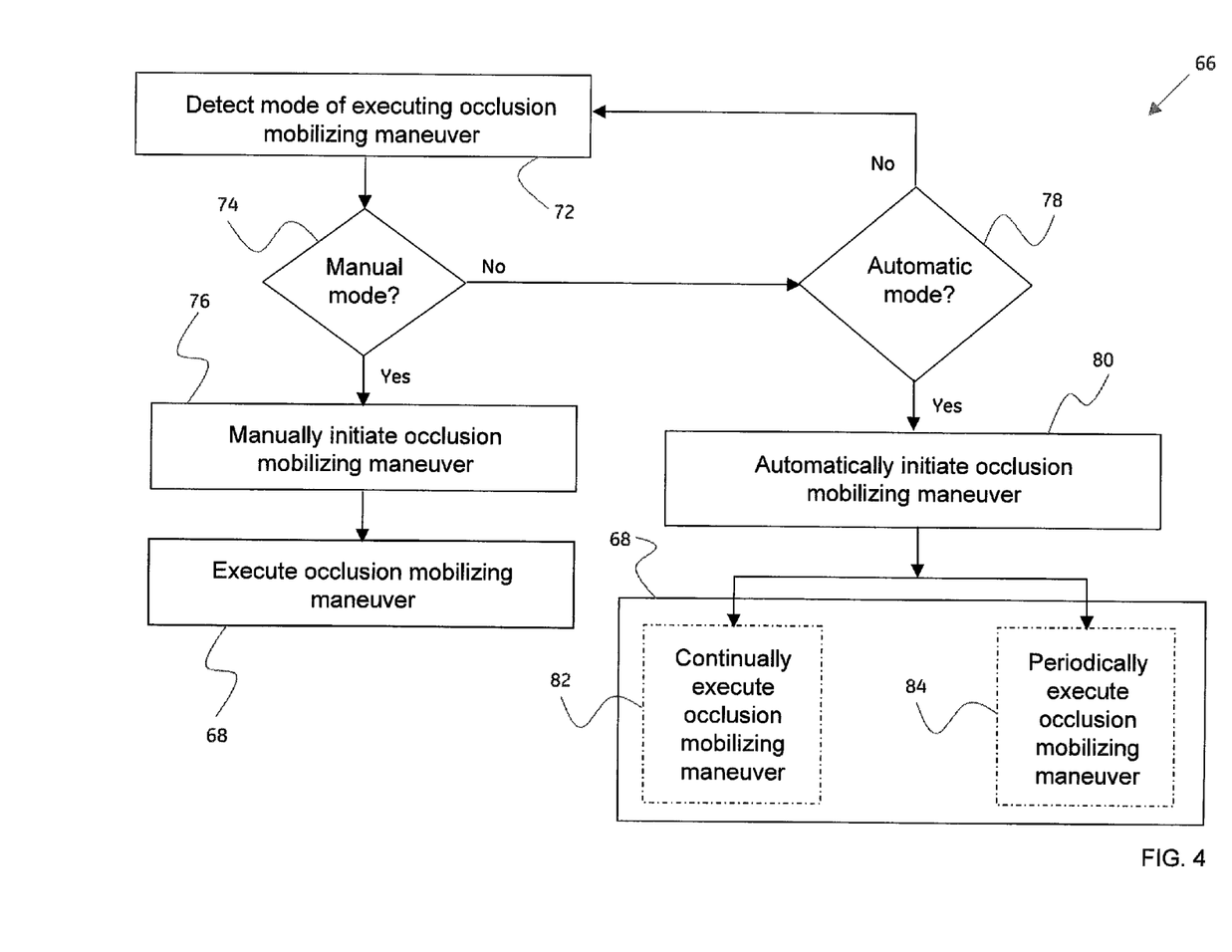
FIG. 4 is a flow chart illustrating an exemplary method for initiating mobilization of occlusions from a breathing tube using the exemplary ventilation system of FIG. 1, in accordance with aspects of the present technique.

Step 66 may be better understood with reference to FIG. 4. Referring now to FIG. 4, a flow chart depicting the process of step 66 (see FIG. 3) is depicted. As noted hereinabove, the maneuver for mobilizing the occlusion from the breathing tube may be manually initiated by the clinician or may be automatically initiated. Accordingly, the method may start at step 72, where a mode of executing the occlusion mobilizing maneuver may be detected. Furthermore, in accordance with aspects of the present technique, the occlusion mobilizing maneuver may be initiated either manually or automatically. Accordingly, at step 74, a check may be carried to verify if the mode of executing the occlusion mobilizing maneuver includes a manual mode. At step 74, if it is verified that the mode of executing the occlusion mobilizing maneuver includes a manual mode, then the occlusion mobilizing maneuver may be manually initiated, as depicted by step 76. In one embodiment, the occlusion mobilizing maneuver may be manually triggered by the clinician.

However, if at step 74, it is verified that the mode of executing the occlusion mobilizing maneuver does not include a manual mode, then another check may be carried out at step 78 to verify if the mode of executing the occlusion mobilizing maneuver includes an automatic mode. At step 78, if it verified that the mode of executing the occlusion mobilizing maneuver includes an automatic mode, then the occlusion mobilizing maneuver may be automatically initiated as indicated by step 80. In one embodiment, the occlusion mobilizing module 16 (see FIG. 1) may be configured to automatically trigger execution of the occlusion mobilizing maneuver. Further, in accordance with exemplary aspects of the present technique, in the automatic mode of operation, the occlusion mobilizing maneuver may be continually executed, as indicated by step 82. Alternatively, the occlusion mobilizing maneuver may also be periodically executed as depicted by step 84. In the periodic mode of executing the occlusion mobilizing maneuver, the maneuver may be periodically executed at predetermined time intervals.

With returning reference to FIG. 3, once the mode of executing the occlusion mobilizing maneuver is detected at steps 72-74, and 78 (see FIG. 4), the occlusion mobilizing maneuver may be executed, as indicated by step 68. As noted hereinabove, the occlusion mobilizing maneuver may be configured to aid in mobilizing any occlusions in the breathing tube associated with the patient 12 (see FIG. 1). The exemplary occlusion mobilizing maneuver may be better understood with reference to FIG. 5.

Figure 5:
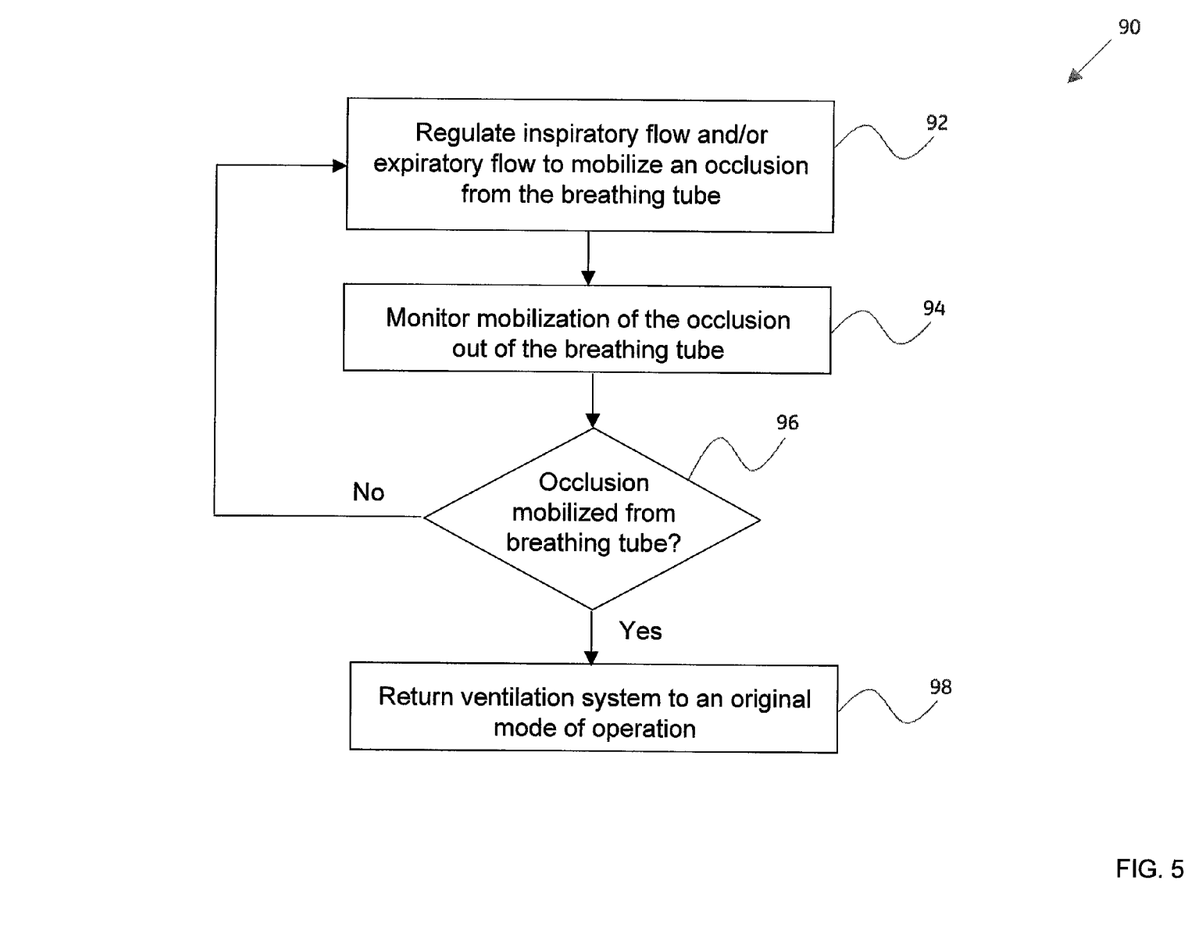
FIG. 5 is a flow chart illustrating an exemplary occlusion mobilizing maneuver for mobilizing occlusions from a breathing tube, in accordance with aspects of the present technique.

Turning now to FIG. 5, a flow chart 90 depicting the exemplary method of mobilizing one or more occlusions from a breathing tube coupled to a patient is illustrated. The method starts at step 92, where an inspiratory flow, an expiratory flow, or a combination thereof may be regulated in order to facilitate automatic mobilization of one or more occlusions from the breathing tube. As previously noted, the breathing tube, such as the breathing tube 18 (see FIG. 1) may be configured to operationally couple the patient, such as the patient 12 (see FIG. 1), to a ventilation system, such as the ICU ventilator 14 (see FIG. 1). More particularly, at step 92, in accordance with exemplary aspects of the present technique, the inspiratory flow, the expiratory flow, or a combination thereof, may be regulated such that a peak expiratory flow is greater than a peak inspiratory flow to facilitate the automatic mobilization of the occlusion from the breathing tube. Step 92 may be better understood with reference to FIG. 6.

Figure 6:
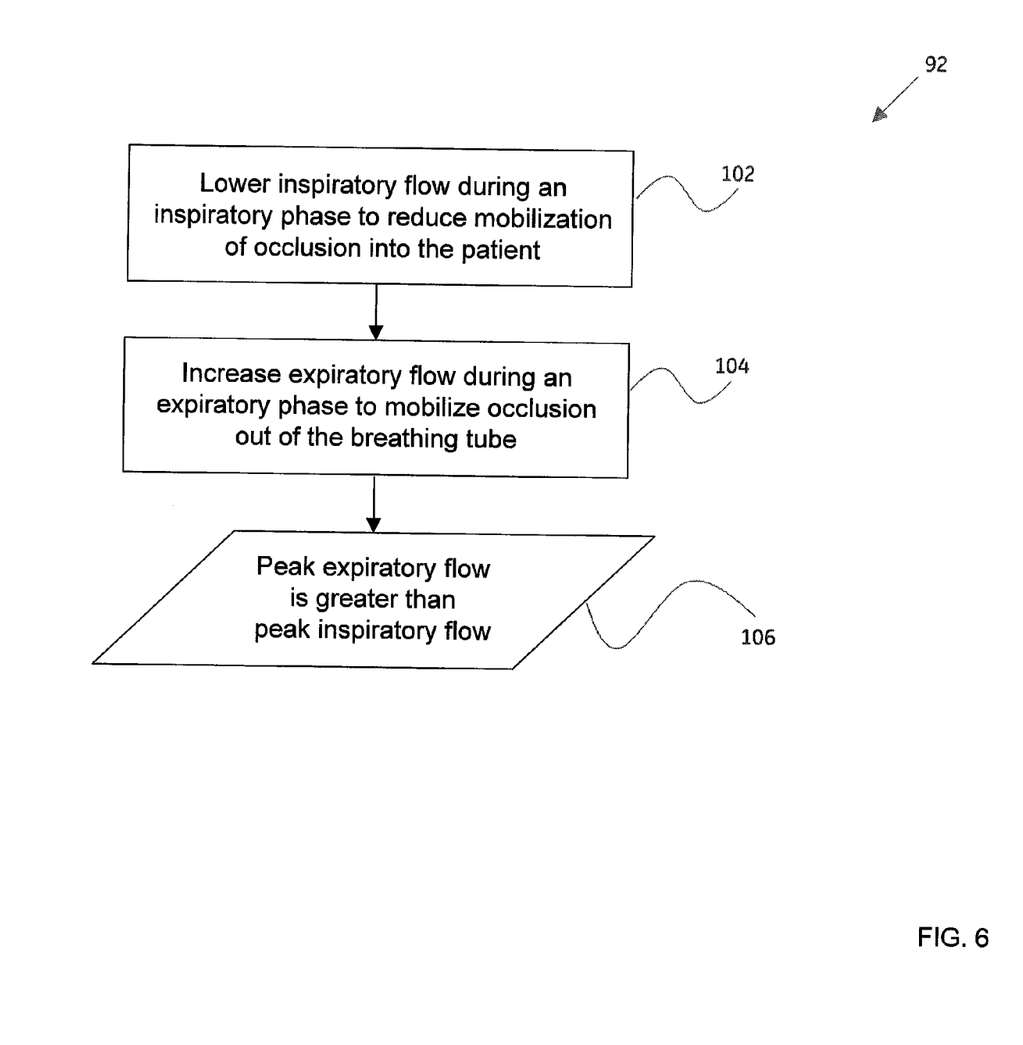
FIG. 6 is a flow chart illustrating an exemplary method for regulating inspiratory flow and/or expiratory flow for mobilizing occlusions from a breathing tube, in accordance with aspects of the present technique.

FIG. 6 is a flow chart depicting the exemplary method of regulating the inspiratory flow, the expiratory flow, or a combination thereof, to automatically mobilize the occlusion from the breathing tube. More particularly, the inspiratory flow and/or the expiratory flow may be regulated such that a peak expiratory flow during an expiratory phase of a respiratory cycle of the patient 12 (see FIG. 1) is greater than a peak inspiratory flow during an inspiratory phase of the respiratory cycle of the patient.

The method starts at step 102, where an inspiratory flow may be lowered to aid in reducing mobilization of the occlusion into the patient 12 (see FIG. 1). More particularly, the inspiratory flow during an inspiratory phase of a respiratory cycle of the patient 12 may be lowered. In one embodiment, the inspiratory flow during the inspiratory phase of the respiratory cycle may be lowered by temporarily turning off airway resistance compensation during the inspiratory phase. Additionally, a pressure rise time may also be enhanced to aid in lowering the inspiratory flow during the inspiratory phase.

Furthermore, as indicated by step 104, an expiratory flow may also be increased to aid in mobilizing the occlusion from the breathing tube. In other words, the expiratory flow during an expiratory phase of the respiratory cycle of the patient 12 may be enhanced. More particularly, the expiratory flow during the expiratory phase may be increased, while the inspiratory flow during the inspiratory phase may be lowered such that the peak expiratory flow is greater than the peak inspiratory flow, as indicated by reference numeral 106.

It may be noted that the presence of any occlusions in the breathing tube disadvantageously results in increased resistance in the breathing tube. Accordingly, in one embodiment, the ICU ventilator 14 (see FIG. 1) may be configured to compensate for the increased resistance in the breathing tube by lowering an airway pressure target to a value below a positive end expiratory pressure (PEEP), thereby enhancing the expiratory flow during the expiratory phase of the respiratory cycle of the patient 12. In accordance with aspects of the present technique, the pressure measuring subsystem 28 (see FIG. 1) may be utilized to monitor lung pressure associated with the patient 12. More particularly, the pressure measuring subsystem 28 may be used to monitor the lung pressure to ensure that the lung pressure does not drop below a predetermined PEEP value.

Additionally, in accordance with further aspects of the present technique, the expiratory flow during the expiratory phase may be increased by actively sucking out the gas from the lungs of the patient 12, thereby facilitating active exhalation of gas from the lungs of the patient 12. In certain embodiments, a High Frequency Oscillatory Ventilation (HFOV) system (not shown in FIG. 1) may be employed to aid in the active exhalation of gas from the lungs of the patient 12, and thereby facilitate increased expiratory flow during the expiratory phase.

In accordance with further aspects of the present technique, a suction subsystem (not shown in FIG. 1) may be used to aid in dropping the pressure in the breathing tube faster than conventional means. It may be noted that use of the suction subsystem may also aid in dropping the pressure in the breathing tube to negative pressure values. Here again, the pressure measuring subsystem 28 may be employed to ensure that the lung pressure does not drop below the predetermined PEEP value. Furthermore, in accordance with aspects of the present technique, any occlusions in the breathing tube may be mobilized out of the breathing tube and into water traps of the breathing tube.

With returning reference to FIG. 5, consequent to step 92, the occlusion in the breathing tube may be mobilized out of the breathing tube and into the water traps of the breathing tube, for example. In order to ensure that the detected occlusion has indeed been mobilized out of the breathing tube, it may be desirable to monitor the mobilization of the occlusions out of the breathing tube. Accordingly, the mobilization of the occlusion from the breathing tube may be monitored, as indicated by step 94. In one embodiment, the mobilization of the occlusions out of the breathing tube may be monitored by monitoring tube resistance of the breathing tube. Alternatively, flow and pressure waveform patterns may also be monitored to monitor the mobilization of occlusions from the breathing tube.

In certain other embodiments, a combination of monitoring of the breathing tube resistance and monitoring of the flow and pressure waveform patterns may be employed to aid in monitoring the mobilization of the occlusion from the breathing tube. Accordingly, a check may be carried out at step 96 to determine if the occlusion has been mobilized from the breathing tube. If it is determined that the occlusion has been mobilized from the breathing tube, then the ventilation system 10 (see FIG. 1), and more particularly the ICU ventilator 14 (see FIG. 1) may be returned to a previous mode of operation, as indicated by step 98. In other words, once the occlusion mobilizing maneuver has been successfully executed, the ICU ventilator 14 may be returned to the previous mode of operation. In one embodiment, the previous mode of operation of the ICU ventilator 14 may include providing artificial ventilation to the patient. Furthermore, the airway resistance compensation that had been temporarily turned off may be resumed. Also, as previously noted, the pressure rise time may be increased to aid in lowering the inspiratory flow during the inspiratory phase during the execution of the occlusion mobilizing maneuver. Here again, once the occlusion is mobilized out of the breathing tube, the current pressure rise time may be reset to the value of the pressure rise time employed prior to the execution of the occlusion mobilizing maneuver. It may be noted that at step 96 if it is verified that the occlusion has not been mobilized out of the breathing tube, then control may be returned to step 92, where the inspiratory flow and/or the expiratory flow may be regulated to mobilize the occlusion out of the breathing tube.

The method for mobilizing one or more occlusions from the breathing tube and the system for mobilizing one or more occlusions from the breathing tube described hereinabove dramatically simplify clinical workflow by advantageously facilitating automatic mobilization of occlusions in the breathing tube. Moreover, by regulating the inspiratory flow and/or the expiratory flow in the patient, the occlusion may be automatically mobilized out of the breathing tube, thereby resulting in a less invasive, more comfortable method of mobilizing occlusions from the breathing tube in the patient. Furthermore, employing the exemplary method for mobilizing the occlusion from the breathing tube advantageously facilitates reduction in the frequency of clinician intervention to clear lung secretions building up in the breathing tube.

While only certain features of the invention have been illustrated and described herein, many modifications and changes will occur to those skilled in the art. It is, therefore, to be understood that the appended claims are intended to cover all such modifications and changes as fall within the true spirit of the invention

The invention claimed is:

1. A method of mobilizing an occlusion from a breathing tube, comprising automatically mobilizing the occlusion from the breathing tube by regulating an inspiratory flow and an expiratory flow by lowering the inspiratory flow and increasing the expiratory flow such that a peak expiratory flow is greater than a peak inspiratory flow to mobilize the occlusion from the breathing tube, wherein the breathing tube is configured to operationally couple a patient to a ventilation system, and wherein the ventilation system is configured to provide artificial respiration to a patient.

2. The method of claim 1, wherein the artificial respiration provided to the patient includes airway resistance compensation, and wherein lowering the inspiratory flow comprises temporarily turning off airway resistance compensation during an inspiratory phase of the patient.

3. The method of claim 1, wherein lowering the inspiratory flow comprises increasing pressure rise time during the inspiratory phase of the patient.

4. The method of claim 1, wherein increasing the expiratory flow comprises lowering an airway pressure target to a value below a predetermined pressure value during an expiratory phase of the patient.

5. The method of claim 4, wherein the predetermined pressure value comprises a positive end expiratory pressure value.

6. The method of claim 1, wherein increasing the expiratory flow comprises using high frequency oscillatory ventilation to increase the expiratory flow during an expiratory phase of the patient.

7. The method of claim 1, further comprising monitoring lung pressure.

8. The method of claim 7, wherein monitoring lung pressure comprises monitoring breathing tube resistance, monitoring flow waveform patterns, monitoring pressure waveform patterns, or combinations thereof.

9. The method of claim 8, further comprising initiating mobilization of the occlusion from the breathing tube.

10. The method of claim 9, wherein initiating mobilization of the occlusion from the breathing tube comprises detecting a mode of initiating mobilization of the occlusion from the breathing tube.

11. The method of claim 10, wherein the mode of initiating mobilization of the occlusion from the breathing tube comprises a manual mode of initiating mobilization of the occlusion from the breathing tube, an automatic mode of initiating mobilization of the occlusion from the breathing tube, or a combination thereof.

12. The method of claim 11, wherein the manual mode of initiating mobilization of the occlusion from the breathing tube comprises manually initiating mobilization of the occlusion from the breathing tube in response to a trigger signal, wherein the trigger signal is generated in response to detection of the occlusion from the breathing tube.

13. The method of claim 11, wherein the automatic mode of initiating mobilization of the occlusion from the breathing tube comprises continually mobilizing the occlusion from the breathing tube.

14. The method of claim 11, wherein the automatic mode of initiating mobilization of the occlusion from the breathing tube comprises mobilizing the occlusion from the breathing tube at predetermined time intervals.

15. The method of claim 1, further comprising detecting presence of the occlusion in the breathing tube.

16. The method of claim 15, further comprising monitoring mobilization of the occlusion from the breathing tube.

17. The method of claim 16, further comprising returning the ventilation system to an original mode of operation on completion of mobilization of the occlusion from the breathing tube.

18. An integrated ventilation system, comprising:
a ventilation system configured to provide artificial respiration to a patient, wherein the ventilation system is operationally coupled to the patient via a breathing tube; and
an occlusion mobilizing module that detects an occlusion in the breathing tube and generates a trigger signal indicative of the detected occlusion, the occlusion mobilizing module, in response to the generated trigger signal, further reduces the inspiratory flow and increases the expiratory flow such that a peak expiratory flow is greater than a peak inspiratory flow to automatically mobilize an occlusion from the breathing tube.

19. The integrated ventilation system of claim 18, further comprising a pressure measuring subsystem that monitors flow and pressure waveforms measured from the breathing tube to monitor the mobilization of the occlusion.

20. The integrated ventilation system of claim 19, further comprising a suction subsystem that is pneumatically connected to the breathing tube and the suction subsystem operates during an expiratory phase to reduce pressure in the breathing tube.

21. The integrated ventilation system of claim 20, wherein the pressure measuring subsystem further monitors a lung pressure and the suction subsystem is operated such that the monitored lung pressure is not below a predetermined PEEP value.

* * * * *